United States Patent [19]
Zuckermann et al.

[11] Patent Number: 6,033,631
[45] Date of Patent: Mar. 7, 2000

[54] SYNTHESIZER WITH REAGENT RECYCLING

[75] Inventors: Ronald N. Zuckermann, Berkeley; Kiet Truong, San Jose; Selina DeRose-Juarez, Rohnert Park; Katy Shang-Chi Kuey, Cerritos; Matthew Geoffrey Owings, Santa Rosa, all of Calif.; Benjamin Joseph Ver Steeg, Albuquerque, N.Mex.; Henry Chin, Apple Valley, Calif.

[73] Assignee: Chiron Corporation, Emeryville, Calif.

[21] Appl. No.: 09/067,932

[22] Filed: Apr. 28, 1998

Related U.S. Application Data

[60] Provisional application No. 60/044,338, Apr. 28, 1997.
[51] Int. Cl.[7] .............................. C08F 5/02; G05B 17/00
[52] U.S. Cl. ......................... 422/131; 422/116; 422/236; 422/135; 435/287.3; 935/88
[58] Field of Search ..................... 422/131, 132, 422/292, 116, 135; 935/88; 436/48; 435/287.3

[56] References Cited

U.S. PATENT DOCUMENTS

| | | | |
|---|---|---|---|
| 4,671,941 | 6/1987 | Niina et al. .............................. | 422/131 |
| 5,240,680 | 8/1993 | Zuckermann et al. ..................... | 422/67 |
| 5,362,447 | 11/1994 | Nokihara ................................ | 422/131 |
| 5,395,594 | 3/1995 | Nokihara et al. ....................... | 422/135 |
| 5,681,534 | 10/1997 | Neves ..................................... | 422/131 |
| 5,792,431 | 8/1998 | Moore et al. ........................... | 422/134 |

FOREIGN PATENT DOCUMENTS

| | | |
|---|---|---|
| 592968 | 4/1994 | European Pat. Off. . |
| WO 82/03076 | 9/1982 | WIPO . |
| WO 96/40202 | 12/1996 | WIPO . |

OTHER PUBLICATIONS

Figliozzi et al., "Synthesis of N–Substituted Glycine Peptoid Libraries", *Methods in Enzymology* 267:437–447, 1996.
Derwent Publication No. AN 95–167247 (XP002075684) Database WPI, entitled "Peptide Synthesis Apparatus for Continuously Synthesizing Peptide(s) Efficiently Comprises Continuous Flow . . ." Apr. 4, 1995.

*Primary Examiner*—Robert J. Warden, Sr.
*Assistant Examiner*—James Kennedy
*Attorney, Agent, or Firm*—Robins & Associates; Sharon M. Fujita; Robert P. Blackburn

[57] ABSTRACT

An apparatus is provided for conducting solid phase oligomer synthesis. The apparatus includes a reaction vessel in which a solid phase support is contained. The reaction vessel has a top opening through which gases and solvents can be delivered by way of a series of conduits and valves. The reaction vessel is interconnected through a bottom opening therein and through a series of conduits and valves with a vessel or series of vessels containing a reagent or series of reagents, respectively, required for the synthetic reaction. The reagent vessel serves a both a source of reagent delivered to the reaction vessel and as a repository for unused reagent returned thereto from the reaction vessel. Reagent delivery and mixing is gas-driven using an associated source of an inert gas.

9 Claims, 4 Drawing Sheets

SYNTHESIZER WITH REAGENT RECYCLING

CROSS-REFERENCE TO RELATED APPLICATION

This application claims the benefit of U.S. provisional application Ser. No. 60/044,338, filed Apr. 28, 1997, which is incorporated herein by reference.

TECHNICAL FIELD

The invention relates generally to solid phase chemical synthesis. More particularly, the invention relates to a novel method and apparatus for use in chemical synthesis technologies for the production of individual peptoids and peptoid libraries utilizing solid phase organic chemistries.

BACKGROUND OF THE INVENTION

Oligomeric N-substituted glycines (NSG) and other "peptoids" are polymers that are well suited for the generation of diverse molecular libraries. These molecules can be prepared using conventional solid phase synthetic technologies that have been developed for the production of other polymers such as proteins. For example, methods are generally known for use in preparing defined polypeptides using Merrifield solid phase synthetic schemes. Merrifield (1963) *J. Am. Chem. Soc.* 85:2149–2154; Tam et al. (1987) *The Peptides*, Academic Press (New York), pp. 185–249. Another well-known method for achieving solid-phase peptide synthesis uses 9-fluorenylmethoxycarbonyl (Fmoc) protecting groups on the amino acids. Meienhofer et al. (1979) *Int. J. Pept. Protein Res.* 13:35, Atherton et al. (1979) *Bioorg. Chem.* 8:351. In this technique, the peptide is immobilized on any of a wide variety of commercially available polystyrene resins. Wang, S. (1973) *J. Am. Chem. Soc.* 95:1328, Mergler et al. (1988) *Tetrahedron Lett.* 29:4005, Albericio et al. (1987) *Int. J. Pept. Protein Res.* 30:206. The synthesis of individual peptoid oligomers can be carried out using equipment and techniques adapted from the above-referenced peptide syntheses. Simon et al. (1992) *Proc. Natl. Acad. Sci. USA* 89:9367.

Methods for the systematic synthesis of a multiplicity of polymers to screen for pharmacological or biological activity have also been developed. Particularly, combinatorial libraries can be prepared containing a large number of molecules using "resin-splitting" or "mix/split" techniques. Furka et al. (1991) *Int. J. Peptide Protein Res.* 37:487–493; Lam et al. (1991) *Nature* 354:82–84. Resin mixing/splitting methodology can also be used to generate peptoid libraries. Figliozzi et al. (1996) *Methods in Enzymol.* 267:437.

Although these methods of synthesis may be routine, they are quite laborious. The difficulty in conducting such syntheses becomes magnified when it is necessary to prepare many specified molecules in parallel, e.g., in the synthesis of combinatorial libraries. Accordingly, a number of automated systems for the synthesis of polypeptides and/or peptoid oligomers have been developed. One automated system described in Schnorrenberg et al. (1989) *Tetrahedron* 45:7759 relates to the synthesis of peptides on resin using several automated arms to withdraw solvent from a reaction vessel, add a solvent, wash and to mix reagents. Another automated system described in U.S. Pat. No. 5,240,680 to Zuckermann et al. relates to the synthesis of polypeptides using an apparatus having structure for automated transfer of reaction solutions into and out of a cleavage vessel, transfer of peptide solution from the cleavage vessel to the extraction vessel, and transfer of extraction solvent into and out of the extraction vessel. These automated systems have been modified (e.g., software modifications) for use in large scale peptoid syntheses.

The use of such automated systems in synthetic oligomer and polymer production schemes avoids a great deal of manipulation and increases the efficiency of synthetic polymer production. However, in the production of peptoids, a large amount of unused reagents are wasted in the synthetic processes, since such reagents are generally used iteratively and in excess (to increase reaction rate and overall yield) during the process.

Accordingly, there remains a need for a method and apparatus to synthesize peptoid oligomers using solid phase synthesis techniques, which avoids the waste associated with prior systems.

SUMMARY OF THE INVENTION

In one embodiment of the invention, a method for conducting chemical syntheses involving a sequence of reaction steps to be conducted on a solid phase is provided. More particularly, a method for synthesizing a peptoid oligomer is provided which entails the steps of: (a) providing a solid phase having a protected amine group; (b) deprotecting the amine group on the solid phase to provide a reactive amine; (c) acylating the reactive amine by contacting said amine with an acyl submonomer to provide an acylated amine containing a leaving group; (d) displacing the leaving group from the acylated amine with a primary amine by contacting the acylated amine with an amine reagent to provide an N-substituted monomer and a leaving group by-product; and (e) recycling unused amine reagent with the leaving group by-product to a containment means, thereby providing a recycled amine reagent suitable for use in a subsequent displacement reaction.

In another embodiment, an apparatus for synthesizing oligomers immobilized on solid phase particles in a particle suspension is provided. The apparatus comprises a reaction vessel, a first delivery means for delivering a gas and/or a solvent into the reaction vessel through a top opening, and a second delivery means for conducting the following operations through a bottom opening in the reaction vessel: (i) delivering a gas into the reaction vessel to effect mixing of the particulate suspension; (ii) removing fluids from the reaction vessel; (iii) introducing a reagent into the reaction vessel from an associated reagent vessel; and (iv) returning unused reagent from the reaction vessel to the associated reagent vessel. Control means connected to the first and second delivery means effect control over the operation of the apparatus.

In another embodiment, an apparatus for synthesizing oligomers immobilized on solid phase particles in a particle suspension is provided. The apparatus includes a reaction vessel, a first delivery means communicating with a top opening of the reaction vessel and enabling delivery of a gas and/or a solvent into the reaction vessel therethrough, a reagent vessel, a second delivery means communicating with the reagent vessel and a bottom opening of the reaction vessel, wherein the second delivery means enables the following operations through the bottom opening of the reaction vessel: (i) delivering a gas into the reaction vessel to effect mixing of the particulate suspension; (ii) removing fluids from the reaction vessel; (iii) introducing a reagent into the reaction vessel from the reagent vessel; and (iv) returning unused reagent from the reaction vessel to the reagent vessel. A control means connected to the first and second delivery means can be used for controlling the operation thereof.

Additional objects, advantages and novel features of the invention will be set forth in part in the description that follows, and in part will become apparent to those skilled in the art upon examination of the following, or may be learned by practice of the invention.

DETAILED DISCLOSURE OF THE INVENTION

Figure 1:
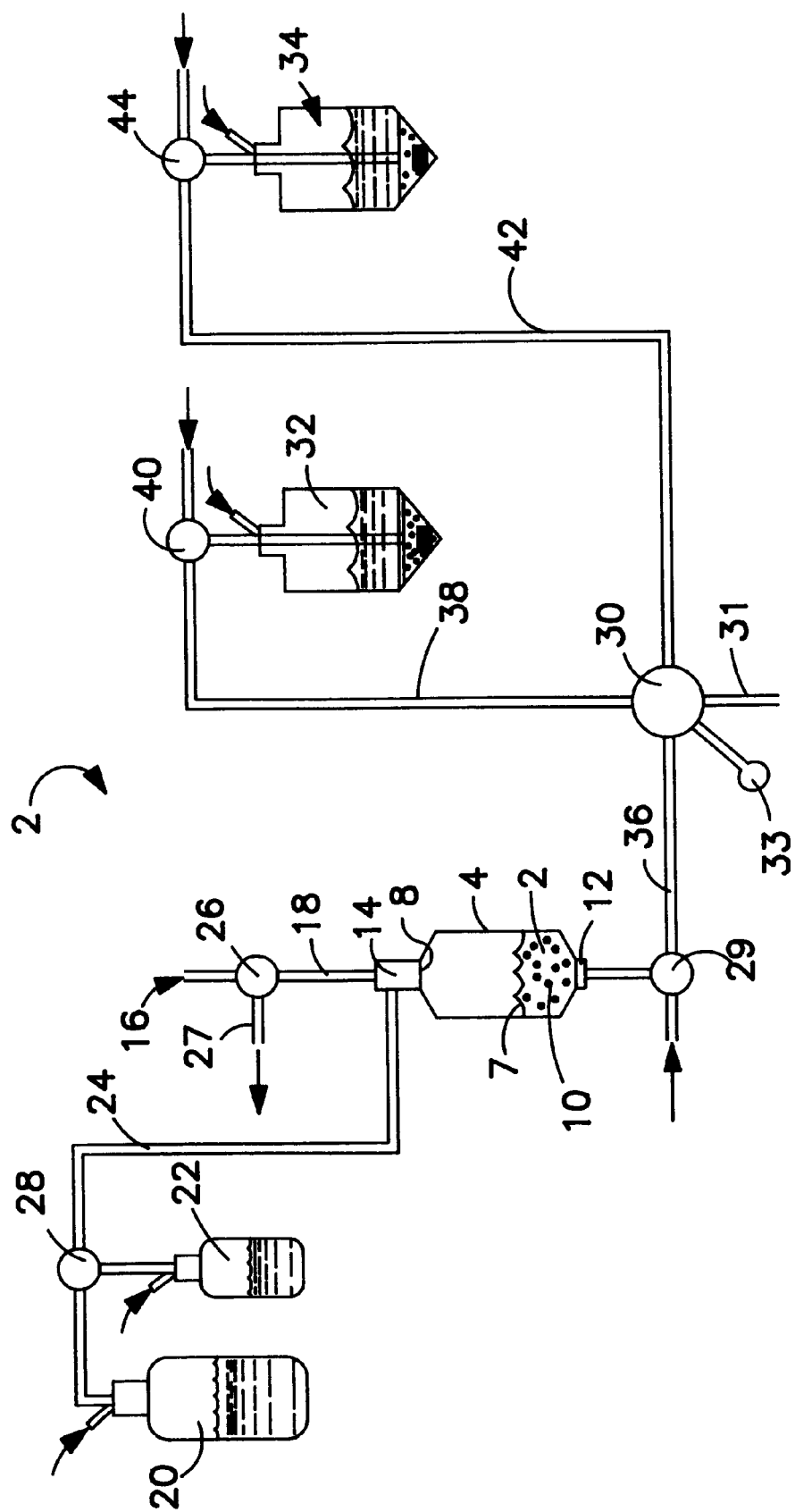
FIG. 1 is a schematic representation of an apparatus for use in the practice of the methods of the invention.

The practice of the methods of the present invention will employ, unless otherwise indicated, conventional techniques of solid-phase synthesis, including peptoid synthesis, peptide synthesis and other solid phase organic chemistries that are within the skill of the art. Such techniques are explained fully in the literature. See, e.g., Thompson et al. (1996) "Synthesis and Applications of Small Molecule Libraries," *Chem Rev.* 96:555–600; Terrett et al. (1995) "Combinatorial Synthesis—The Design of Compound Libraries and Their Application to Drug Discovery," *Tetrahedron* 51(30):8135–8173; Kirk-Othmer's *Encyclopedia of Chemical Technology*; House's *Modern Synthetic Reactions*; C. S. Marvel and G. S. Hiers' text, ORGANIC SYNTHESIS, Collective Volume 1; *Oligonucleotide Synthesis* (M. J. Gait, ed., 1984); International Publication No. WO 96/40202.

All patents, patent applications, publications and other types of references cited herein, whether supra or infra, are hereby incorporated by reference in their entirety.
A. Definitions Before the present invention is disclosed and described in detail, it is to be understood that this invention is not limited to specific method formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a reaction vessel" includes two or more such vessels, reference to a solvent reservoir includes two or more reservoirs, and the like.

In this specification and in the claims which follow, reference will be made to a number of terms which shall be defined to have the following meanings:

The term "monomer" as used herein refers to a chemical entity that may be covalently linked to one or more other entities to form an oligomer. Monomers are subunits that include, for example, amines, amino acids, nucleotides, saccharides, alkylators, nucleophiles, and the like.

The term "oligomer" includes polymers such as poly NSGs and other peptoids (i.e., N-substituted polyamides) as described in International Publication No. WO 96/40202, which are produced by the method of the invention, and which include homopolymers, copolymers and interpolymers of any length. Thus, oligomers may be comprised of a single repeating monomer, two alternating monomer units, two or more monomer units randomly and/or deliberately spaced relative to each other. Oligomers produced in the practice of the invention are comprised of 2–100 monomers, more preferably 2–50 monomers.

The term "acyl submonomer" refers to an acylating reagent which comprises a reactive carbonyl or carbonyl equivalent, and a leaving group which may be displaced in a nucleophilic displacement by an amine. "Carbonyl or carbonyl equivalent" includes, without limitation, carboxylic acids, esters, amides, anhydrides, acyl halides, and isocyanates. Esters and amides used will generally be "reactive" forms, e.g., DIC adducts and the like. The acyl submonomer may further comprise a side chain. Suitable acyl submonomers include, without limitation, bromoacetic acid (BrAA), 3-bromopropionic acid, 2-bromopropionic acid, 2-bromoethylisocyanate, 2-bromoethylchloroformate, 6-phenyl-3-bromohexanoic acid, 4-bromomethyl-benzoic acid, 4-bromomethyl-2-methoxybenzoic acid, 5-bromomethyl-pyridine-2-carboxylic acid, and the like.

The term "solid phase" intends any solid support or substrate on which the reaction steps of chemical syntheses involving a sequence of reaction steps can be carried out. Thus, the term includes particulate substrates such as resins which have traditionally been employed in standard Fmoc chemical syntheses, including, without limitation, polystyrene resins and 1% cross-linked polystyrene resins, polyacrylamide resins, grafted poly(propylene) or poly(ethylene) resins, PEG-polystyrene resins, and the like.
B. General Methods The present invention is based on the discovery of a novel method and associated apparatus for preparing peptoid oligomers. The method and apparatus provide for the recycle of amine reagents during the synthetic process which greatly reduces reagent consumption.

Peptoids are synthetic N-substituted polyamide biopolymers having a structure generally similar to proteins which can be used to generate chemically diverse libraries of novel molecules. Exemplary peptoids include oligomers of N-substituted glycine. The monomers may incorporate t-butyl-based side-chain and 9-fluorenylmethoxy-carbonyl α-amine protection. The assembly of monomers into peptoid oligomers is currently performed, for example, on a solid phase using the submonomer method of Zuckermann et al. (1991) *J. Am. Chem. Soc.* 114:10646. See also International Publication No. WO 96/40202.

In the submonomer method for producing peptoids, syntheses are typically conducted with Rink amide polystyrene resin (Rink et al. (1987) *Tetrahedron Lett.* 28:3787). Resin-bound amines are typically acetylated by in situ activation of a haloacetic acid (e.g., bromoacetic acid) with diisopropylcarbodiimide. Subsequently, the resin-bound acetamides (e.g., bromoacetamide) are displaced by addition of an amine. The amines may incorporate acid-labile protection of additional acid reactive groups, for example using t-butyl-based protection. This two-step cycle is repeated until the desired number of monomers is added. The oligopeptoid is then released from the resin by treatment with 95% trifluoroacetic acid/5% water. The syntheses can be performed using automated equipment, such as a robotic synthesizer. See, e.g., Zuckermann et al. (1992) *Pept. Protein Res.* 40:498.

In the submonomer method for preparing peptoids, amine reagents are generally added to the growing oligopeptoid chain at a concentration of about 0.5–3M, preferably 1–2M, for each reaction step to increase the reaction rate and overall synthesis yield. This typically translates to a molar equivalent of about 10–40, more preferably about 20 equivalents. The need to use these reagents in excess results in a significant waste of materials, as large amounts of the unused amine reagents are lost with each step in the synthetic process. Thus, in a first embodiment of the invention, a submonomer method for synthesizing peptoids is provided which allows for the recycle and subsequent reuse of unused amine reagents. The ability to recycle unused amine reagents during peptoid syntheses significantly reduces the consumption of such reagents, particularly in the production of high molecular weight peptoids.

More particularly, in the submonomer method of the invention, the addition of each monomer entails an acylation step, e.g., the addition of an acyl submonomer such as bromoacetic acid (BrAA), and a displacement step, e.g., addition of an amine reagent. The peptoid synthesis begins with a particle suspension containing a suitable solid phase, for example, an amine resin. Deprotection of the amine group on the resin is carried out using a suitable organic solvent such as piperidine/dimethyl formamide (DMF) to provide a reactive amino resin. The amino resin is then acylated with the acyl submonomer reagent. Nucleophilic displacement of the acyl submonomer leaving group is then carried out with a primary amine to build, e.g., an N-substituted glycine (NSG) monomer. After displacement, unused amine reagent is returned to a storage vessel for use in subsequent rounds of displacement. These acylation, displacement and recycle steps are carried out in an iterative fashion to produce a desired oligomer. Those of ordinary skill in the art will readily recognize that substrate-bound acyl submonomer can also be used as the initial starting material instead of amine resin. Subsequent displacement of the acyl leaving group with an amine is thus the first step followed by acylation with a second acyl submonomer and so on. The submonomer method is described in International Publication Nos. WO 96/40202 and WO 94/06541 which publications are incorporated herein by reference in their entireties.

Wash solvents, e.g., dimethyl formamide (DMF) and dimethyl sulfoxide (DMSO) are generally used between acylation and displacement steps. Particularly, before an acylation step is carried out, the solid phase is generally washed several times with DMF solvent and thoroughly drained before addition of the diisopropylcarbodiimide (DIC) and haloacetic acid (e.g., BrAA) reagents. In like manner, before each displacement step, the solid phase is washed with DMF and DMSO and thoroughly drained before addition of the amine building block.

The only by-product that is generated during the displacement reaction is one equivalent of a leaving group by-product, such as, for example, HX, where X is a halogen from an acyl halide (e.g., HBr). Accordingly, in the present method, regeneration of the amine reagent is carried out in the storage vessel by scavenging, for example, an HX contaminant with an inorganic base or ion-exchange resin. Typically, the scavenging agent will comprise a neutralizing resin or organic base such as KOH; however, other suitable agents include, but are not limited to, $K_2CO_3$, $Na_3PO_4$, or $Ca(OH)_2$; binding agents; basic alumina resins; DOWEX anion exchange resins; cross-linked polysaccharide resins with basic amino groups; or like materials.

In another embodiment of the invention, an apparatus for synthesizing oligomers is provided. The apparatus can be used to carry out the submonomer method described above, and includes means for recycling reagents, such as, for example, amine reagents. Referring to FIG. 1, a submonomer synthesizer apparatus with reagent recycling is generally indicated at 2. The apparatus comprises a reaction vessel 4 in which oligomers are synthesized in a particle suspension 6 formed with the solid phase particles. The reaction vessel has a top opening 8 for receiving fluids, including gases, and a bottom opening 10 having a suitable filter means 12 disposed therein through which nonparticulate fluids may freely pass.

The reaction vessel can be comprised of any suitable material selected for chemical inertness and physical resiliency. Thus, the reaction vessel can be comprised of a borosilicate such as PYREX®, or any other suitable material generally used in the construction of chemical reaction containers. Borosilicate materials are generally preferred. Further, the reaction vessel 4 can comprise external threads disposed around the periphery of the top and/or bottom openings 8 and 10 to facilitate liquid- and pressure-tight fluid communication throughout the vessel using a threaded cap. Alternatively, the top and/or bottom openings can be provided with a shoulder, lip, or like sealing surface, with or without an optional O-ring gasket, for mating with a suitable lid or friction-type coupling.

The filter means 12 physically retains the solid support, e.g., the resin on which a peptoid is synthesized, while allowing for the draining and/or introduction of solvents, reagents, and mixing or driving gases. Thus, the filter means can be comprised of any material capable of retaining common solid supports on which chemical syntheses are conducted. The filter substrate material should also be chemically inert with respect to the reagents used in the chemical syntheses conducted in the reaction vessel, durable, reusable and generally nondeformable over multiple uses. The particular substrate used to provide the filter means will generally have a mesh size ranging from about 10 to about 60 $\mu$m, although much larger mesh sizes may be suitable for use in syntheses where larger supports are used. In one particular vessel, the filter means 12 is in the form of a course glass frit having, for example, a 40 to 60 $\mu$m filter size.

A first delivery means communicates with the top opening 8 of the reaction vessel 4, and provides for the delivery of gas and/or one or more solvents into the reaction vessel via the top opening. The first delivery means can be comprised of multiple components, such as the delivery means depicted in FIG. 1. Specifically, the first delivery means can comprise a multi-position valve 14 which switchably communicates the top opening 8 with an associated source of gas 16 via conduit 18, and associated solvent containers 20 and 22 via conduit 24. Actuation of the valve 14 to a first position, then, allows for the introduction of driving gas into the reaction vessel 4 from the associated gas source.

Suitable driving gases are those inert gases commonly used in solid phase syntheses, such as nitrogen, helium, argon, or the like. An additional valve 26 arranged between the gas source 16 and the valve 14 allows for the introduction of gas into the reaction vessel, or the venting of gas from the reaction vessel via vent port 27. Another valve 28 arranged between the solvent containers 20 and 22, and the valve 14 allows for delivery of solvents and/or reagents into the reaction vessel, for example, delivery of diisopropylcarbodiimide (DIC) and BrAA into the reaction vessel during an acylation step.

Referring still to FIG. 1, the apparatus 2 also includes a second delivery means that allows a number of operations to be conducted through the bottom opening 10 of the reaction vessel 4. In particular, the second delivery means allows for (i) the delivery of a gas into the reaction vessel to effect mixing of the particulate suspension 6, (ii) removal of solvents and other fluids from the reaction vessel, (iii) introduction of amine reagents into the reaction vessel during displacement steps, and (iv) return of unused amine reagents to an associated reagent container after a displacement step has been carried out.

The second delivery means can comprise a number of alternative combinations of elements. In FIG. 1, the second delivery means comprises a multi-positional valve 30 which switchably communicates the bottom opening 10 of the reaction vessel between first and second associated reagent vessels, respectively indicated at 32 and 34. The valve 30 also switchably communicates the bottom opening 10 with a suitable waste port 31.

In operation for the synthesis of peptoids, acylation reagents (e.g., DIC and BrAA) and washing solvents (e.g., DMF and DMSO) are drained from the vessel to waste after an acylation step has been carried out in the reaction vessel. Drainage of the vessel is carried out by actuation of the valve 30 to a first position that communicates the bottom of the reaction vessel with the waste port via conduit 36 and valve 29. If desired, a driving gas can be introduced into the reaction vessel from the top opening 8 thereof using the first delivery means as described above.

For a first displacement step, then, the valve 30 is actuated to a second position that allows for the delivery of amine reagent from the first reagent vessel 32 to the reaction vessel 4. The amine reagent travels through conduit 38, to the valve 30, and passes therefrom into the reaction vessel via the bottom opening 10 and through filter means 12. An additional valve means 40 allows the first reagent vessel 32 to be pressurized to drive reagent into the reaction vessel, with the concomitant actuation of valve 26 to a venting position. Actuation of the valve 30 to a closed position retains the amine reagent within the reaction vessel for the duration of the displacement step. Mixing or agitation of the solid phase can be conducted by actuating the valve 30 to another position that communicates a source of mixing gas 33 with the bottom opening 10. The mixing gas can be used both as an effervescent to evacuate fluids from the valve and conduit, as well as to agitate or mix the contents of the reaction vessel.

Delivery of the reagent through the bottom of the reaction vessel provides for additional mixing and agitation of the solid phase particles which have been retained by the filter means 12. After displacement has been carried out for a suitable time, unused amine reagent is returned to the reagent vessel 32 by actuating the valve 30 back to the second position and allowing the reagent to drain back into the reagent vessel. A driving gas can be introduced into the reaction vessel via the top opening 8 to help drive the unused reagent back into its respective vessel. In addition, the reagent vessel 32 can be vented via the valve means 40, and the reaction vessel pressurized via valve 26 to help drive the return of the unused reagent. After washing the solid phase with an appropriate solvent which is drained to waste (e.g., DMF), the solid phase is ready for the next acylation step.

The reagent vessel can be provided with a scavenging agent to eliminate contaminating by-products generated during the displacement step, e.g., HBr. Thus, the reagent is available for subsequent use in another displacement step. After acylation has been conducted, and solvents drained from the reaction vessel, the valve 30 is actuated to a third position that allows for the delivery of a second amine reagent from the second reagent vessel 34 into the reaction vessel 4. The second amine reagent travels through conduit 42, to the valve 30, and passes therefrom into the reaction vessel via the bottom opening 10. An additional valve means 44 allows the second reagent vessel 34 to be pressurized to drive reagent into the reaction vessel. After the displacement step has been effected, unused amine reagent is returned to the second reagent vessel as described with respect to the first reagent vessel. As will be readily appreciated by those skilled in the art after reading this specification, any number of different reagent vessels can be communicated with the reaction vessel using a similar combination of valves and actuation steps.

In the apparatus 2 depicted in FIG. 1, fluid flow within the instrument is driven by a pressurized gas delivery system. Other motive systems are suitable for use with the invention, such as pump- or vacuum-driven systems known in the art. However, a pressurized gas-driven system is preferred due to the requirement for less components than necessary with a pump-driven system. As such, valves 14, 28, 30, 40, and 44 are generally multipositional solenoid valves as commonly employed with organic chemical syntheses. These valves can further be coated with polytetrafluoroethylene (e.g., TEFLON®) or a like material to provide resistance to the solvents and organic reagents used in the methods of the invention. Actuation of the valves can be effected by way of a control means connected to the first and second delivery means. Such control means can comprise a suitable microprocessor which is programmed for various diverse oligomer syntheses, and can also control temperature, pressure and fluid level sensors which allow for automatic monitoring of syntheses and correction of minor errors therein. Alternatively, some or all of the valve manipulations can be conducted manually.

The conduits 24, 36, 38, and 42 are comprised of suitable chemically resistive materials, for example polytetrafluoroethylene (TEFLON®) or polyether ester ketone (PEEK). Couplings between the various conduits, valves and vessels are generally liquid- and pressure-tight, for example snap couplings (e.g., SWAGELOCK® fittings), ferrules and/or threaded closures that are also comprised of suitable chemically inert materials.

A single source of pressurized gas can be used to move liquids around within the apparatus 2, as well as to provide for mixing of the reagents in the reaction vessel. The particular gas used in the system is a matter of choice; however, nitrogen, helium, or argon are preferred.

Figure 2:
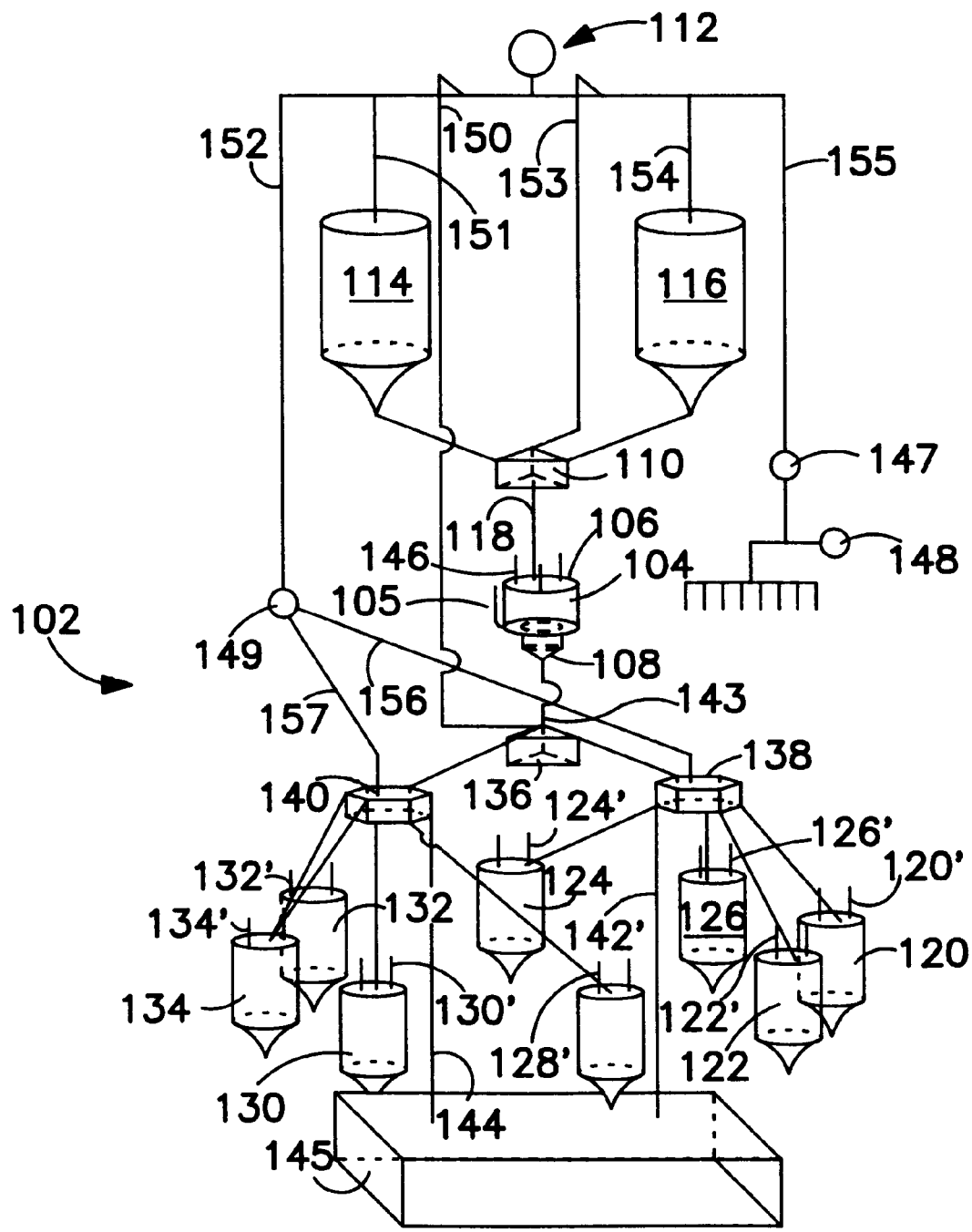
FIG. 2 is a pictorial representation of an alternative apparatus embodiment according to the present invention.

An alternative apparatus for synthesizing oligomers is depicted in FIG. 2. The apparatus 102 is designed to operate along the same lines as the apparatus of FIG. 1, wherein solvents, reagents and gases are introduced into a reaction vessel via top and bottom openings, and unused reagents are recycled between the reaction vessel and storage vessels in the practice of the submonomer method described herein.

The apparatus 102 has a reaction vessel 104 having a top opening 106 and bottom opening 108 as described above. A particle suspension including solid phase particles can be introduced into the reaction vessel, and subsequent iterative acylation and displacement steps, for example, can be carried out to produce synthetic peptoid oligomers. The top opening 106 communicates with a first delivery means that provides for delivery of gas or solvents into the reaction vessel through the top opening. In the system depicted in FIG. 2, the first delivery means comprises multipositional valve 110 which can be used to interconnect gas from an associated gas manifold, generally indicated at 112, and associated valves 147–149 and lines 150–157, or first and second solvents from first and second solvent vessels, 114, and 116, respectively, with the reaction vessel 104 via the top opening. For example, the solvent vessels 114 and 116 can be used to supply DMF and DMSO washing solvents to the reaction vessels between acylation and displacement steps in a representative peptoid synthesis. In this particular system configuration, the valve 110 can be a four position solenoid valve with a common outlet 118 that communicates with the reaction vessel. This type of valve provides switchable control over whether the reaction vessel is pressurized with gas, or filled with one of the two solvents from the associated solvent vessels.

The apparatus 102 further includes a plurality of reagent vessels, 120–134 which have vent ports/20'/34' which are selectively communicated with the reaction vessel 104 via a second delivery means via port 143 which is in fluid communication with the bottom opening 108 of the reaction vessel via port 143. Each reagent vessel is used to house a single reagent. Reagents for use in the method include acylation reagents (e.g., DIC and BrAA), and several different displacement reagents (e.g., amines 1–6).

The second delivery means depicted in FIG. 2 is comprised of the operative combination of three multipositional valves. In particular, a multipositional valve 136 with a common inlet that communicates with the bottom opening 108 of the reaction vessel provides switchable control over whether a mixing gas stream from the gas manifold 112 is bubbled up through the bottom opening of the reaction vessel, or a selected reagent from one of the reagent vessels 120–134 is delivered via first or second associated multipositional valves 138 and 140. Each of the associated valves 138 and 140 also has a port, 142 and 144, respectively, which leads to waste 145, providing two alternative paths with which to drain the reaction vessel 104.

Operation of the apparatus 102 proceeds as described above, wherein actuation of various combinations of valves allows for solvent introduction and removal from the reaction vessel, and for the introduction of reagents (e.g., amine), and subsequent return of unused reagent from and to selected reagent vessels. Actuation of the valves can be manually, or controlled by a control means such as a microprocessor.

One representative acylation and displacement series is conducted using the apparatus 102 as follows. DMF solvent from solvent vessel 114 is added to the reaction vessel 104 to rinse the vessel and the solid phase by actuation of the valve 110 to a first position and venting of the reaction vessel through vent port 146 which allows delivery of the solvent into the reaction vessel. The valve 110 is then actuated to a second position to allow introduction of gas from manifold 112 and valves 136 and 138 are actuated to provide a drainage path for the used solvent.

After sufficient rinsings with the DMF solvent and subsequent drainage of spent solvent, the DIC and BrAA acylation reagents from reagent vessels 132 and 134, respectively, are introduced into the reaction vessel 104 via the bottom opening 108 by actuation of valve 140 between two different positions to select each reagent, actuation of valve 136 to a first position to provide an appropriate delivery path to the reaction vessel, and venting of the reaction vessel through vent port 146. After the acylation reagents have been added, valve 136 can be actuated to a second position to communicate a mixing gas through the bottom opening of the reaction vessel to provide for mixing and agitation of the solid phase.

When acylation is completed, valve 136 is actuated back to its first position, and valve 140 is actuated to a third position to provide a drainage path to waste via waste port 144. The reaction vessel, and the acylated solid substrate contained therein, are then washed by several additions of the DMF solvent as described above, and a subsequent wash with the DMSO solvent from the solvent vessel 116. Delivery of solvent from vessel 116 is carried out by actuating the valve 110 to a third position and actuation of the vent port 146 which combination allows delivery of the solvent into the reaction vessel, and then the combination of actuating the valve 110 back to its second position to allow introduction of gas from manifold 112, and actuating valves 136 and 138 to provide a drainage path for the used solvent.

Once the solid phase has been washed and drained, displacement with an amine reagent from reagent vessel 120 is carried out. In particular, the amine reagent is introduced into the reaction vessel 104 via the bottom opening 108 by actuation of valve 138 to a first position and actuation of valve 136 back to its first position to provide a delivery path to the reaction vessel. Suitable mixing of the reagent can be conducted as above by actuating the valve 136 to its second position and introducing the mixing gas. Unused amine reagent is then returned to vessel 120 by actuating valves 136 and 138 to their first positions, and pressurizing the reaction vessel using the first delivery means.

A number of different valve combinations can be used to carry out the above described method. Further, additional cycles using one or more different amine regents can be used until a desired peptoid oligomer is obtained. After a final displacement reaction and solvent rinsing, the solid phase can be washed with dichloromethane and then cleaved, or dried in vacuo and then stored before cleavage.

The choice of materials for use in the apparatus 102 is again dictated by the need to provide inert, resilient surfaces which contact the solvents and reagents used in the submonomer method of the invention. A single source of gas, e.g., pressurized nitrogen, can be used to direct fluid movement throughout the system. The gas manifold 112 can thus be comprised of any suitable material such as copper, TEFLON®, or the like, and pressurized gas can be supplied to the manifold through a multistage pressure regulator or like controlling means. Further, a number of different valve combinations can be used to direct one or more solvents through the various valves and conduits of the system to remove residual reagents and prevent carry over or contamination of downstream or subsequent operations.

Figure 3:
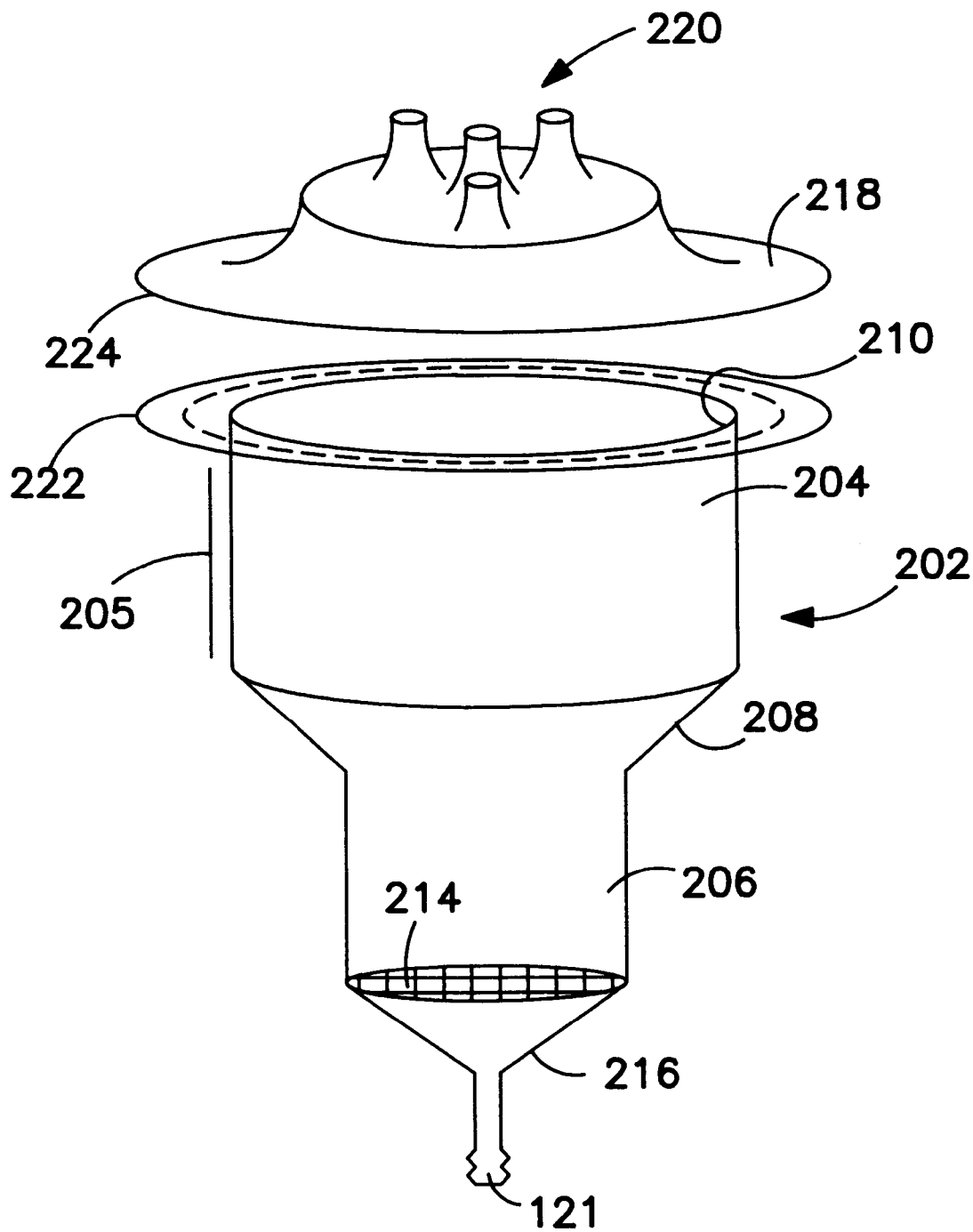
FIG. 3 is a side view of a reaction vessel for use in the synthesizing systems of the invention.

A number of different reaction vessel configurations can be used in the synthesis systems depicted in FIGS. 1 and 2. However, one preferred reaction vessel configuration is depicted in FIG. 3. The reaction vessel, generally indicated at 202 has a cylindrical upper portion 204, a cylindrical lower portion 206 and a shoulder portion 208 connecting the upper and lower portions. The upper portion 204 has a larger diameter than the lower portion 206, and the shoulder portion 208 provides a deaggregating shoulder which helps disperse aggregates of solid phase particles, and also prevents foam caused by bubbling of the mixing gas into the reaction vessel through the bottom opening 212 thereof.

At the bottom of the reaction vessel, a filter means 214 covers the bottom opening 212. The filter means 214 allows passage of nonparticualte fluids through the bottom opening, but is selected to have a suitable porosity to retain the growing oligomer in the reaction vessel during rinsing and draining operations. In the embodiment depicted in FIG. 3, the filter means comprises a glass frit having a porosity of 40 m which is sufficient to retain solid phase resins having a diameter of approximately 100 m or greater. The filter means 214 is also selected to provide a surface area sufficient to promote rapid draining of the solid phase slurry.

The lower portion 206 of the reaction vessel also contains a diffuser section 216 having a reducing diameter which reaches a minimum at the bottom opening 212. The diffuser section allows the mixing gas which is bubbled up through the bottom of the vessel to contact and mix solid phase over the entire surface of the filter means 214, rather than just a portion in the center of the filter. External threads disposed around the bottom opening of the reaction vessel allow for positive, liquid- and pressure-tight coupling with a conduit and/or delivery means.

The top opening 210 of the reaction vessel is closed by a lid 218 which includes a plurality of communication ports, generally indicated at 220. These ports allow for liquid- and pressure-tight coupling with conduits, delivery means, purging valves, and optional measuring devices, e.g. pressure transducers, thermometers, or the like which allow pressure and temperature within the vessel to be monitored as described above.

The lid 218 can be attached to the reaction vessel by resilient coupling means that cooperate with mating flanges 222 and 224, respectively disposed on the vessel and lid as indicated in the Figure. A suitable sealing gasket, such as an 0-ring can be used to provide a pressure-tight seal.

In some oligomer syntheses, it may be desirable to conduct one or more steps at elevated temperatures. Accordingly, in any of the apparatus configurations described herein above, an optional temperature control device 7, 105 or 205 can be used to effect temperature changes in the reaction vessel. For example, a Peltier device can be contacted with the outside of a reaction vessel (e.g., 4, 104, or 202) to provide acute control over the temperature in the reaction vessel. Other temperature control means, such as heating coils or elements can be used in a like manner to provide varying temperatures of up to 100° C. within reaction vessels. Optional temperature monitoring equipment can be used as described above, and heating or cooling can be controlled by a microprocessor, or manually by the operator of the apparatus.

Figure 4:
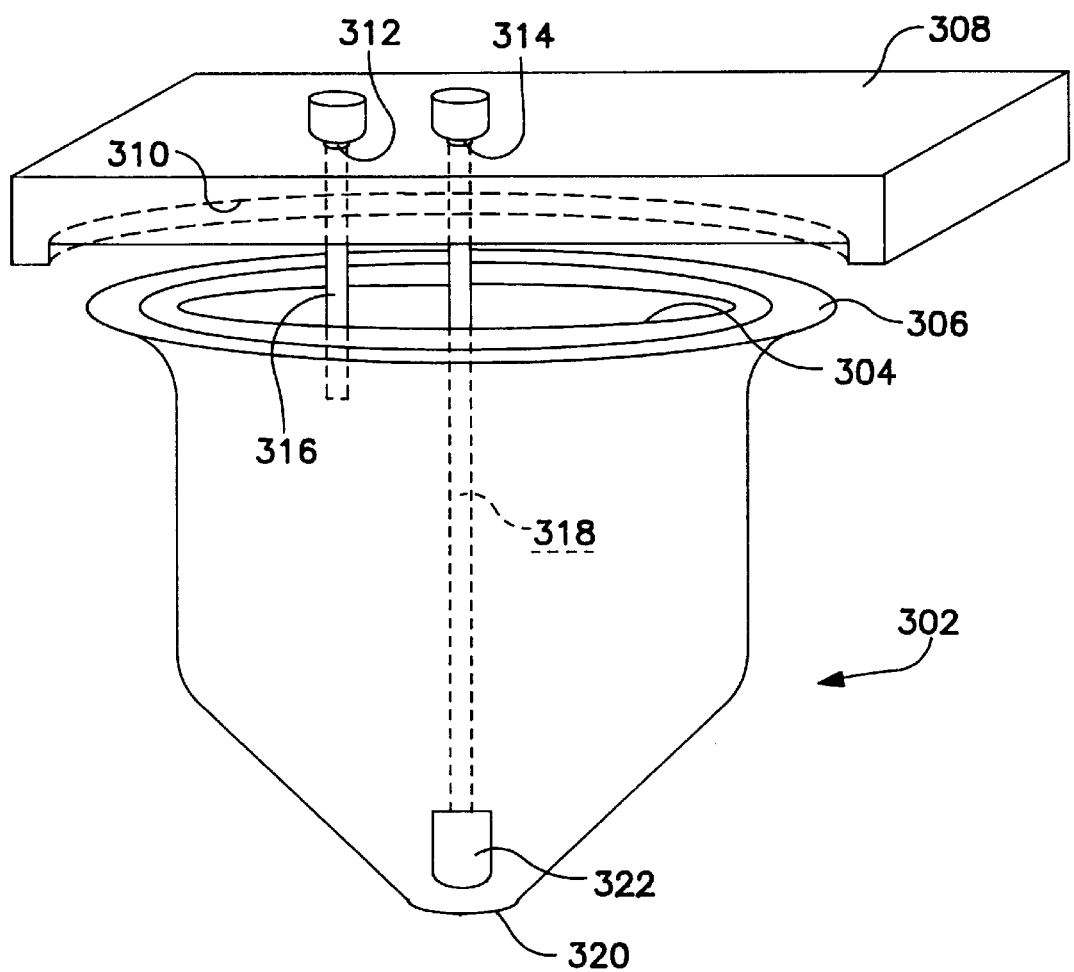
FIG. 4 is a side view of a reagent vessel which can be used in oligomer syntheses which include a reagent recycling step.

Various different reagent vessel configurations can also be used in the synthesis systems depicted in FIGS. 1 and 2. One preferred reagent vessel configuration for use in the method and synthesis systems of the invention is shown in FIG. 4. The reagent vessel 302 has a top opening 304 which has a sealing surface 306 provided around its periphery for interfacing with an associated lid. The lid 308 contains a corresponding sealing surface 310 which is used to provide a pressure-tight seal when closed against the sealing surface 306 at the top of the reagent vessel.

Two communication ports, 312 and 314 disposed in the lid 308 provide access to the contents of the reagent vessel when the lid is coupled to the reagent vessel by a suitable resilient connector such as a spring clip, tensioned clamp or the like. An O-ring gasket can also be provided to ensure a pressure-tight seal. A first conduit 316 is disposed within the communication port 312 and provides a coupling lead for connection to a source of gas which is used to pressurize the vessel for delivery of a reagent therefrom. A second conduit 318 is disposed within the communication port 314 and extends substantially to the bottom 320 of the reagent vessel 302. The conduit 318 communicates the contents of the reagent vessel with the second delivery means as described above with reference to the discussion of FIGS. 1 and 2. In operation, the reagent is drawn up into the synthesis system for delivery to a reaction vessel by pressurizing the reagent vessel 302 with a suitable driving gas via the conduit 316, and allowing the reagent to pass through the conduit 318 into the system. The bottom 320 of the reagent vessel 302 can be configured to have a substantially tapering or conical shape to minimize the volume of inaccessible reagent contained within the reagent vessel.

After a reaction has been conducted with, for example, an amine reagent (e.g., displacement), unused reagent, along with by-product contaminants, is returned to the vessel using a reverse displacement operation, e.g., by venting the reagent vessel via the conduit 316 and collecting the returned reagent. Once in the reagent vessel, contaminating by-product (e.g., HBr) can be scavenged using a suitable scavenging agent.

The scavenging agent is typically a neutralizing resin or organic base such as KOH. However, other suitable agents include, but are not limited to, $K_2CO_3$, $Na_3PO_4$, or $Ca(OH)_2$; binding agents; basic alumina resins; DOWEX anion exchange resins; cross-linked polysaccharide resins with basic amino groups; or like materials. Particulate scavenging agents having a suitable particle size, e.g., KOH or DOWEX® resins, can be added directly to the reagent vessel. In such cases, the conduit 318 can be fitted on its most downstream portion with a suitable reagent filter means 322. Such a filter means 322 will generally comprise a cylindrical stainless steel or polytetrafluoroethylene (Teflon®) frit having a 10–50 m filter size which prevents travel of the scavenging agent into the rest of the apparatus plumbing and hardware where it could contaminate the rest of the synthesis system and/or cause physical blockage of the system.

A number of alternative filtering methods are available when scavenging agents having a fine particle size are used in the reagent vessel. For example, a closed packet of scavenging agent can be provided wherein the packet is permeable to nonparticulate fluids, but has a sufficiently small pore or mesh size so as to limit the travel of the agent from the packet. This particular method can be coupled with the provision of the filter means 322, or used in place thereof.

Reagent vessels used in the methods and systems of the present invention, such as the vessel 302, can be provided in a number of different volume sizes depending on the particular reagent used, and the oligomer synthesis conducted. One preferred reagent vessel is designed to handle 1 liter of the reagent solution. In the synthesis of a 50mer peptoid molecule containing a single amine group, for example, wherein the synthesis is carried out in a 150 mL reaction vessel using a 1 to 3M amine reagent solution, approximately 800 mL of the amine solution will be required, taking into account the recycling feature of the invention. Thus, provision of a reagent vessel for use in peptoid synthesis which contains 1000 mL of the amine reagent provides some flexibility in synthesis since the maximum calculated volume of reagent needed in the synthesis of a 50 mer peptoid is exceeded by approximately 25%.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

We claim:

1. An apparatus for synthesizing oligomers immobilized on solid phase particles in a particle suspension, said apparatus comprising;
   (a) a reaction vessel having a top opening for receiving fluids and gases, and a bottom opening having filter means through which nonparticulate fluids may freely pass;
   (b) first delivery means for delivering a gas and/or solvent into the reaction vessel through the top opening;

(c) second delivery means for conducting the following operations through the bottom opening (i) delivering a gas into the reaction vessel to effect mixing of the particulate suspension, (ii) removing fluids from the reaction vessel; (iii) introducing a reagent into the reaction vessel from an associated reaction vessel, and (iv) returning unused reagent from the reaction vessel to the associated reagent vessel, and (d) control means connected to the first and second delivery means for controlling the operation thereof.

2. The apparatus of claim 1, wherein the second delivery means can be used to switchably communicate the bottom opening of the reaction vessel between two or more discrete associated reagent vessels to enable the delivery, and subsequent return, of a reagent from and back to each respective reagent vessel.

3. The apparatus of claim 2, wherein the second delivery means comprises an operative combination of multi-position valves which communicate the bottom opening of the reaction vessel with a source of gas, a waste port, and two or more associated reagent vessels.

4. The apparatus of claim 1, wherein the first delivery means can be used to switchably communicate the top opening of the reaction vessel with two or more associated solvent sources.

5. The apparatus of claim 4, wherein the first delivery means comprises an operative combination of multi-position valves which communicate the top opening of the reaction vessel with a source of gas and two or more associated solvent sources.

6. The apparatus of claim 1, wherein the reaction vessel filter means is comprised of a glass frit.

7. The apparatus of claim 6, wherein the reaction vessel comprises a cylindrical upper portion, a cylindrical lower portion and a shoulder portion connecting said upper and lower portions.

8. The apparatus of claim 7, wherein the upper portion of the reaction vessel has a larger diameter than the lower portion of said vessel.

9. The apparatus of claim 1, further comprising a temperature control means operatively contacted with the reaction vessel and capable of controlling the temperature of the particle suspension within said reaction vessel.

* * * * *